US008362449B2

(12) United States Patent
Matsui et al.

(10) Patent No.: US 8,362,449 B2
(45) Date of Patent: Jan. 29, 2013

(54) TOTAL INTERNAL REFLECTION MICROSCOPE APPARATUS AND METHOD FOR ANALYZING FLUORESCENT SAMPLE

(75) Inventors: Takuya Matsui, Mito (JP); Satoshi Takahashi, Hitachinaka (JP); Takanobu Haga, Kokubunji (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/147,386

(22) PCT Filed: Nov. 30, 2009

(86) PCT No.: PCT/JP2009/006458
§ 371 (c)(1),
(2), (4) Date: Aug. 2, 2011

(87) PCT Pub. No.: WO2010/089829
PCT Pub. Date: Aug. 12, 2010

(65) Prior Publication Data
US 2011/0284769 A1  Nov. 24, 2011

(30) Foreign Application Priority Data
Feb. 3, 2009  (JP) ................................. 2009-022096

(51) Int. Cl.
*G01N 21/64* (2006.01)
*G01N 21/01* (2006.01)

(52) U.S. Cl. .................................. 250/459.1; 250/458.1

(58) Field of Classification Search ............... 250/459.1
See application file for complete search history.

(56) References Cited

U.S. PATENT DOCUMENTS
5,313,264 A * 5/1994 Ivarsson et al. ................. 356/73
5,437,840 A * 8/1995 King et al. ................. 422/82.08
5,633,724 A * 5/1997 King et al. .................... 356/445
(Continued)

FOREIGN PATENT DOCUMENTS
JP   8-62125    3/1996
JP   8-327533   12/1996
(Continued)

OTHER PUBLICATIONS

Daniel Axelrod, et al., Total Internal Reflection Fluorescence Microscopy in Cell Biology, Traffic 2001, pp. 764-774, vol. 2.

(Continued)

*Primary Examiner* — Marcus Taningco
(74) *Attorney, Agent, or Firm* — Antonelli, Terry, Stout & Kraus, LLP.

(57) ABSTRACT

An object of the present invention relates to observation of single molecule fluorescence while temperature of a sample solution is controlled by a temperature controller and intrinsic fluorescence of the temperature controller is avoided, in a total internal reflection microscope. The present invention relates to provision of an opening at areas of the temperature controller through which incident light and reflected light pass, and configuration adopting a material with intrinsic fluorescence lower than that of the other parts, in a total internal reflection microscope including a prism and the temperature controller. The present invention enables intrinsic fluorescence of the temperature controller to be suppressed, which allows highly sensitive fluorescence observation while controlling sample solution temperature with high precision. For instance, this in turn allows the throughput of single molecule DNA sequencing using a total internal reflection microscope to be improved.

17 Claims, 4 Drawing Sheets

U.S. PATENT DOCUMENTS

| | | | |
|---|---|---|---|
| 6,843,963 B1 * | 1/2005 | Jennissen et al. | 422/82.05 |
| 7,023,547 B2 * | 4/2006 | Venkatasubbarao et al. | 356/369 |
| 2002/0154311 A1 * | 10/2002 | Ivarsson | 356/445 |
| 2008/0070323 A1 * | 3/2008 | Hess et al. | 436/514 |
| 2008/0074671 A1 * | 3/2008 | Ohtsuka et al. | 356/455 |
| 2008/0274905 A1 * | 11/2008 | Greene | 506/4 |
| 2011/0007317 A1 | 1/2011 | Ikebukuro et al. | |

FOREIGN PATENT DOCUMENTS

| | | |
|---|---|---|
| JP | 9-311099 | 12/1997 |
| JP | 2009-14496 | 1/2009 |

OTHER PUBLICATIONS

Dennis C. Prieve, et al., Total Internal reflection Microscopy: A Quantitative Tool for the Measurement of Colloidal Forces, Langmuir 1990, 6, pp. 396-403.

K. D. Kihm, et al, Near-wall hindered Brownian diffusion of nanoparticles examined by three-dimensional ratiometric total internal reflection fluorescence microscopy (3-D R-TIRFM), Experiments in Fluids, 37, 2004, pp. 811-824.

Ido Braslavsky, et al., Sequence information can be obtained from single DNA molecules, PNAS, Apr. 1, 2003, pp. 3960-3964, vol. 100, No. 7.

Jonas Korlach, et al., Selective aluminum passivation for targeted immobilization of single DNA polymerase molecules in zero-mode waveguide nanostructures, PNAS, Jan. 29, 2008, pp. 1176-1181, vol. 105, No. 4.

P. B. Conibear & C. R. Bagshaw, A comparison of optical geometries for combined flash photolysis and total internal reflection fluorescence microscopy, Journal of Microscopy, Dec. 2000, pp. 218-229, vol. 200, Pt 3.

Mary N. Teruel, et al., Parallel Single-Cell Monitoring of Receptor-Triggered Membrane Translocation of a Calcium-Sensing Protein Module, Science, Mar. 8, 2002, pp. 1910-1912, vol. 295.

* cited by examiner

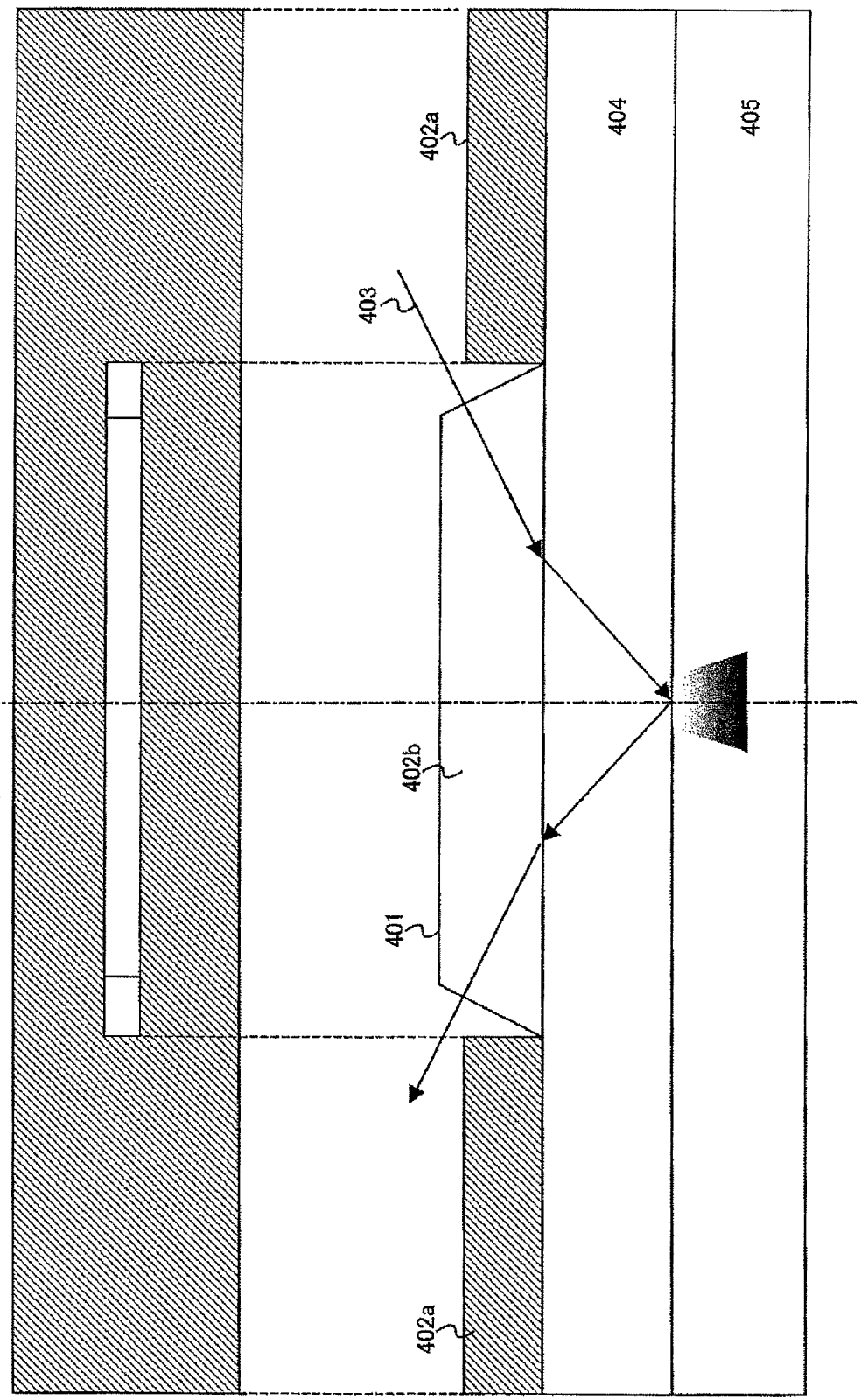

TOTAL INTERNAL REFLECTION MICROSCOPE APPARATUS AND METHOD FOR ANALYZING FLUORESCENT SAMPLE

TECHNICAL FIELD

The present invention relates to temperature control of a total internal reflection microscope.

BACKGROUND ART

Total internal reflection microscopy is an observation method that allows nanoscale local excitation and has a high S/N ratio. The prime characteristics of this method are utilization of evanescent waves caused by total internal reflection of light at a boundary between two materials different in refractive index. When light is incident onto a boundary between a material 1 of refractive index n1 and a material 2 of refractive index n2 from the material 2 of the higher refractive index at a critical angle or more, the light is totally internally reflected at the boundary; this generates evanescent waves, which exponentially decays in the material 1 of the lower refractive index. The evanescent wave is light slightly leaking into a region of an extent of several tens to hundreds of nanometers from the total internal reflection boundary. Accordingly, total internal reflection microscopy generates evanescent waves at the boundary between a fluorescently stained sample and a slide glass, thereby allowing fluorescent observation with a high S/N ratio that is restricted to a significantly small part of the sample adjacent to the slide. This can be applied to single molecule observation.

As to applications utilizing the total internal reflection microscope, Non Patent Literature 1 describes observation of plasma membrane activity and single-molecule events in cell biology fields. Non Patent Literature 2 describes electrical characteristics of colloidal particles in electrochemical fields. Non Patent Literature 3 describes empirical elucidation of Brownian movement. The total internal reflection microscopes thus contribute to many fields. In recent years, application to nucleic acid sequence analysis (DNA sequencing) has been attempted. This will hereinafter be described.

Capillary sequencing, which is a combination of DNA fragment preparation mainly referred to as Sanger method and electrophoresis, is adopted as a present DNA sequencing method. Capillary sequencing has been utilized for human genome analysis and the like, and has yielded great results. However, in consideration of personal genome analysis from viewpoints of tailor-made medical care and the like, a technique has strongly been demanded that allows quick, simple and inexpensive analysis of DNA fragments much longer than those capable of being analyzed by one time of capillary sequencing. Conventional human genome analyses require approximately ten million dollars for analyzing genomes of one person. It is expected that realization of human genome analysis for a thousand dollars, which is a ten-thousandth thereof, dramatically advances applications of sequencing to medical fields. These demands cannot be met only with improvements of the conventional capillary method. Ultimately, if nucleic acids to be analyzed can be sequenced at a single molecule level without nucleic acid amplification, such as PCR, reagent fees become inexpensive because nucleic acid amplification is omitted, and this allows quick and simple sequencing. Further, single molecule sequencing negates the difference in amplification efficiency owing to nucleic acid amplification, thereby allowing highly precise quantification of the number of mRNAs appearing in cells in comparison with the conventional methods. Accordingly, single molecule DNA sequencing based on a novel system has been awaited.

As methods based on novel systems in order to realize this, a method of directly sequencing DNA using a scanning electron microscope, and a nanopore method of sequencing using a fact that voltage values of single strand DNA passing through a nanometer-sized pore are different among nucleotides A, G, C and T have been proposed. However, these methods include many technical problems. Accordingly, it is considered that realization of these methods is difficult.

As promising methods of DNA sequencing replacing these methods, massively parallel analysis methods using an optical technique have been proposed. Apparatuses based on principles of chemiluminescence or fluorescence have already appeared on the market from several companies. Characteristics of these methods are that segmentation of reaction fields using micro beads and micromachining techniques allows massively parallel analysis. Conventional capillary sequencing has improved analysis efficiency by means of multi-channels (to 384). However, the present system also allows massively parallel analysis of hundreds millions units or more, which is much more than the case of capillary sequencing. Accordingly, the readable length of nucleotides is 100 nucleotides or less, which is inferior to capillary sequencing capable of reading almost 1000 nucleotides. However, the throughput is, for instance, 100 nucleotides× hundreds million units ($10^8$), or 10 giga-($10^{10}$) nucleotides per day. Throughput one thousand times that of the capillary method can be expected. Further, the massively parallel analysis reduces the amount of reagent per sample, resultantly reducing the reagent cost. Accordingly, the analysis cost is approximately 100 thousand dollars per human genome of a person, which is approximately one hundredth that of capillary sequencing. However, since these methods amplify nucleic acids to be read and sequence the amplified nucleic acids, it is difficult to further reduce the analysis cost.

In order to attain further reduction in analysis cost, Non Patent Literature 4 has proposed a method of single molecule DNA sequencing according to a massively parallel analysis method using an optical technique. This method will hereinafter be described in detail.

Lasers of wavelengths of 532 and 635 nm are employed and used for detecting fluorescence of phosphors Cy3 and Cy5, respectively. A sample solution is sandwiched between two slide glasses, and then a single target DNA molecule is immobilized on a refractive index boundary surface between the slide glass and the sample solution on the solution side using biotin-avidin binding. Next, primers labeled with Cy3 are introduced in the solution by solution exchange so as to be in a certain concentration, which hybridizes a single Cy3-labeled primer molecule with a target DNA molecule to form a nucleic acid double strand. Subsequently, unreacted Cy3-labeled primer molecule is removed by a cleaning process.

The Cy3-labeled primer molecule hybridized with the target DNA molecule residing at a certain position in the evanescent field. Accordingly, the binding position of the target DNA molecule can be confirmed by detecting fluorescent. In a case where a plurality of Cy3-labeled primer molecules hybridized with the target DNA molecule exist in one scope of the evanescent waves, the entire positions of the Cy3-labeled primer molecules are grasped, thereby allowing subsequent sequencing to be performed in parallel. Further, in a case where a plurality of Cy3-labeled primer molecules hybridized with the target DNA molecule exist in one scope of the evanescent waves and across scopes, the entire positions of the Cy3-labeled primer molecules are grasped while the scope is moved by sliding a stage holding the slide glass, thereby allowing subsequent sequencing to be performed in a massively parallel manner. It is preferable to set the microscope at low power to widen the scope, in order to improve the throughput of sequence analysis. It is also preferable to increase the stage moving speed and to reduce moving time between the scopes incapable of fluorescent observation.

After verification of the positions of all the primer molecules, Cy3 is irradiated with high power excitation light for a certain time to fade fluorescence (quench fluorescence), thereby suppressing subsequent emission of fluorescence. The object of this is to prevent Cy3 in the previous process from being detected when Cy3 is used in and after the following process. In a case where a fluorochrome different from Cy3 is used in and after the following process, the fluorochrome is not necessarily to be quenched. However, there is a possibility that a fluorescent wavelength region of Cy3 overlaps with that of the other fluorochrome. Accordingly, it is preferable to quench the fluorochrome as much as possible.

Next, a solution including an enzyme for adding nucleotides to double-stranded nucleic acids, Cy5 fluorescence-labeled dNTPs (N is one type of A (adenine), C (cytosine), G (guanine) and T (thymine)) is introduced to be in a certain concentration by means of solution exchange. Only in a case of a complementary strand (A and T; C and G) with respect to the target DNA molecule, the fluorescence-labeled Cy5-dNTP molecule is taken into an elongating strand of primer molecules, which is one strand of the double strand nucleic acids. Typically, when the Cy5 fluorescence-labeled dNTP is taken into the elongating strand of the primer molecules, the enzyme tries to take in the next nucleotide. However, a mechanism is adopted in which a certain molecule is preliminarily bound to the position for the nucleotide of the Cy5-dNTP molecule, thereby preventing two nucleotides and more from being consecutively taken in. Subsequently, unreacted Cy5-dNTP molecules are removed by a cleaning operation.

Cy5-dNTPs taken into the elongating strand reside at specific positions in the evanescent field. This allows the binding position of Cy5-dNTP to be verified by detecting fluorescence. Further, identification of a position at which the binding position of Cy5-dNTP and the binding position of the target DNA molecule match with each other allows the sequence of the target DNA molecules immobilized at the prescribed positions in the evanescent field to be read. In a case where a plurality of Cy5-dNTPs taken into the elongating strand of the primer molecules exist in one scope of the evanescent waves, grasping of the positions of all the bound Cy5-dNTPs enables the sequence of the target DNA molecules to be read in parallel. In a case where a plurality of Cy5-dNTPs taken in the elongating strand of the primer molecules exist in one scope of the evanescent waves and across the scopes, grasping of the positions of all the Cy5-dNTPs by moving the stage holding the slide glass to move the scope enables the sequence of the target DNA molecule to be read in a massively parallel manner. It is preferable to set the microscope at low power to widen the scope, in order to improve the throughput of the sequence analysis. It is also preferable to increase the stage moving speed and to reduce moving time between the scopes incapable of fluorescent observation.

After verification of the entire sequence of Cy5-dNTP (one nucleotide), Cy5 is irradiated with high power excitation light for a certain time to fade fluorescence (quench fluorescence), thereby suppressing subsequent emission of fluorescence. In a case where a fluorochrome different from Cy5 is used in and after the following process, the fluorochrome is not necessarily to be quenched. However, there is a possibility that a fluorescent wavelength region of Cy5 overlaps with that of the other fluorochrome. Accordingly, it is preferable to quench the fluorochrome as much as possible. After quenching of Cy5, in order not to consecutively take in two nucleotides or more, the specific molecule bound to the Cy5-dNTP molecule is removed using means such as a catalyst or optical dissociation. This allows the next nucleotide to be elongated.

The above elongation reaction process of Cy5-dNTP is repeated sequentially on four types of nucleotides, for instance such as, dATP→dCTP→dGTP→dTTP→dATP, thereby allowing the nucleotide sequence of the immobilized target DNA molecule to be determined. The elongation reaction process of dNTP enables target DNA molecules to be sequenced in a massive parallel manner. The principle of single molecule sequencing has been described with the example of the fluorochromes of two colors, Cy3 and Cy5. However, fluorochromes are not limited to these two fluorochromes. The technique can be realized by another fluorochrome or a method. For instance, dNTPs are labeled with respective four types of different fluorochromes, negating the need to repeat elongation reaction of the aforementioned four types of nucleotides, dATP→dCTP→dGTP→dTTP→dATP. Accordingly, the throughput becomes four times faster according to a simple calculation. The primer molecules and dNTPs can be labeled with an identical fluorochrome (monochrome).

Non Patent Literature 5 has reported real-time single molecule sequencing as a method of single molecule DNA sequencing with a throughput higher than that of the above literature. Many conventional DNA sequencings utilize a DNA polymerase as an enzyme. However, in the method as with the above literature that performs elongation reaction and sequencing on each nucleotide, the ability that is included in the enzyme and consecutively takes in nucleotides is wasted. The ability of a single molecule of DNA polymerase to take in nucleotides is approximately 1000 nucleotides per second, which is capable of reading over 100 thousand nucleotides and further exerts significantly high fidelity. Thus, two techniques are adopted to consecutively elongate nucleic acid and perform real-time sequencing.

A first technique attaches a phospholinked nucleotide to a distal phosphoric acid, instead of attaching fluorescent labels to nucleotides, and separates the fluorochrome in a process that the enzyme takes in nucleotides. After the nucleotides have thus been taken in, completely natural double strand DNA remains. Fluorescence corresponding to the nucleotide when the enzyme takes in the nucleotide is detected in real-time, thereby allowing consecutive sequencing. Note that it is required to label the four types of nucleotides with different fluorescent labels. Only for a certain time until the enzyme takes in the fluorochrome, the fluorochrome exists at a specific position in the evanescent field. Accordingly, grasping the position at this time allows sequencing. After the fluorochromes are separated according to a second technique, the fluorochromes are adrift in the solution according to the Brownian movement. Accordingly, the fluorochromes do not affect sequencing. In contrast to the method of performing elongation reaction and sequencing on each nucleotide, this method negates the need of the process of quenching the fluorochrome by irradiation with high-power laser.

The second technique is a zero-mode waveguide technique allowing single molecule detection. This technique allows measurement of only a fluorochrome in a nanometer-sized pore. Accordingly, this allows measurement without removing, by a cleaning operation, the fluorochromes separated from the nucleotides and unreacted fluorescently labeled nucleotides not contributing to elongation reaction. These techniques suggest realization of a real-time DNA sequencing.

In a real-time single molecule sequencing, the elongation reaction proceeds consecutively. Accordingly, it is required to fix a normal scope until one sequencing is finished. Thus, in order to improve the throughput, it is effective to set the microscope at low power to widen the scope as much as possible. However, in Non Patent Literature 5, since an objective-type total internal reflection microscope is employed, it is limited to high magnification detection of 60× or more. Two types of total internal reflection microscopes used for single molecule sequencing and the like will hereinafter be described.

A presently used typical total internal reflection microscope is an objective-type total internal reflection microscope. The microscope adopts an inverted arrangement. The objective is positioned below a slide glass via immersion oil. Laser light for generating evanescent waves is obliquely incident from below the slide glass via the objective, thereby generating evanescent waves around a boundary on the slide glass where a sample is disposed. Because a space above the objective can freely be used, this arrangement has characteristics that are excellent in operability and convenience and further capable of acquiring a significantly bright fluorescent image. However, owing to limitation of the principle employing an oil-immersion objective with a high numerical aperture, there is a drawback of limitation to observation with a high magnification of 60× or more.

As another type of total internal reflection microscope without limitation to high magnification observation, a prism type total internal reflection microscope in which a laser is incident via a prism is used. In this microscope, a sample is sandwiched between two slide glasses or a slide glass and a cover glass; the prism is mounted on the upper slide glass; laser light for generating evanescent waves is obliquely incident from above the upper slide glass via the prism; this generates evanescent waves around a boundary of the slide glass contacting with the sample. This arrangement enables the laser light to be efficiently incident, thereby allowing observation with an S/N ratio higher than that of the objective type. Further, in contrast to the objective-type total internal reflection microscope, there is no limitation of magnification. Accordingly, low magnitude observation is also easy. The low magnitude observation widens a scope, thereby improving the throughput, for instance, in Non Patent Literature 5. Therefore, it can be said that the prism type total internal reflection microscope is more suitable than the objective type in view of improvement in throughput. However, in the prism type total internal reflection microscope, a space above the objective is occupied by the prism. Thus, there are drawbacks that operability of the sample and flexibility in arrangement of a specimen are significantly low. It is expected to develop a prism type total internal reflection microscope system that is excellent in operability of a sample and flexibility in arrangement of a specimen, easy to be used together with another optical observation method, and allows low magnitude observation.

Following efforts have been taken in order to improve operability of a sample and flexibility of arrangement of a specimen using a prism type total internal reflection microscope.

First, Non Patent Literature 6 has proposed a system in which an incident prism and an emission prism are cemented onto the undersurface of a slide glass, laser light is introduced into the slide glass from the incident prism to be totally internally reflected in the slide glass in a multiplexed manner, evanescent waves are generated around the upper surface of the slide glass to excite the sample during the multiplexed total internal reflection, the laser light wave-guided by the multiplexed total internal reflection is derived to the outside via the emission prism.

Non Patent Literature 7 has proposed a system in which an end of a slide glass is processed to form an inclined end surface, laser light is introduced into the slide glass from the inclined end surface and totally internally reflected in a multiplexed manner, evanescent waves are generated around the upper surface of the slide glass to excite the sample during the multiplexed total internal reflection, the laser light wave-guided by the multiplexed total internal reflection is derived from an end surface opposite to the inclined end surface to the outside.

These systems have characteristics that the space above the specimen is unoccupied and low magnitude observation is easy. However, since the thickness of the slide glass is limited to approximately 0.2 mm and thin, the number of multiplexed total internal reflections is increased. Accordingly, this tends to generate scattering light owing to the total internal reflections, attenuate wave-guided light, fade fluorescence of a sample, and reduce the S/N ratio. Further, since the incident and emission positions of laser light are fixed, it is required to move the objective in order to change the position of observing a sample and thus the operation is not easy. Accordingly, in a case of a prism type total internal reflection microscope, since a space above the objective is occupied by the prism and the space therebelow is occupied by the objective, operability of a sample and flexibility in arrangement of a specimen are low.

CITATION LIST

Non Patent Literature

Non Patent Literature 1: Alelrod, D. et al vol. 2, pp. 764-774, (2001)
Non Patent Literature 2: Prieve, D. C. and Frej, N. A., Langmuir, 6, pp. 396-403
Non Patent Literature 3: Kihm, K. D. et al., in Fluids, 37, pp. 811-824, (2004)
Non Patent Literature 4: PNAS 2003, Vol. 100, pp. 3960-3964
Non Patent Literature 5: PNAS 105(4): 1176-1181. (2008)
Non Patent Literature 6: Conibear, P. B. and Bagshaw, C. R., Journal of Microscopy, Vol. 200, Pt3, pp. 218-229, (2000)
Non Patent Literature 7: Teruel, M. N. and Meyer, T., Science, Vol. 295, pp. 1910-1912, (2002)

SUMMARY OF INVENTION

Technical Problem

The inventors of this application have devoted to review DNA sequencing using a total internal reflection microscope, and found followings as a result.

It is important for improving the throughput of DNA sequencing to widen the scope capable of detecting at one time. An objective-type total internal reflection microscope is limited to observation with a high magnification of 60× or more. In contrast, since a prism type evanescent system has no limitation of magnification, the throughput is improved by low magnitude observation. For instance, the scope of an objective of 40× is at least twice wider than that of 60×. Accordingly, it is expected that adoption of a prism type total internal reflection microscope improves the throughput at least twice.

In order to improve the throughput, it is also important to increase the reaction rate of the enzyme. It is considered that methods for increasing the reaction rate of an enzyme are not only to elevate substrate concentration and to achieve the optimum pH, but also to achieve the optimum temperature of the enzyme. Among them, the substrate concentration and pH can be realized by changing the composition of the solution. However, control of the optimum temperature (reaction rate) of the enzyme additionally requires a device for controlling temperature. The reaction rate of the enzyme increases with increasing temperature. However, since the enzyme is a protein, the enzyme is denatured at high temperatures. Accordingly, enzyme activity decreases inversely. Typically, animal enzymes are active between 40 and 50° C., and plant enzymes are active between 50 to 60° C. However, there are enzymes active between 80 to 90° C. as with in thermophilic bacteria (90° C. or more in hyperthermophilic bacteria). As described above, it can be considered that adoption of a prism type total internal reflection microscope with a temperature control function allows the throughput as an apparatus to be maximized.

Temperature control systems in prism type total internal reflection microscopes can be broadly classified into air temperature control and local temperature control. The air temperature control is a method of controlling air temperature in a cabinet whose temperature to be kept, using a heating or cooling device and the temperature control cabinet. This method has high temperature stability. However, there are problems that it takes long time to reach a certain temperature and that it is difficult to achieve temperatures of 60° C. or more. In a case of using the cabinet for air temperature control in the prism type total internal reflection microscope, if, for instance, all of a microscope stage holding a slide glass, a prism and an objective are covered, adverse effects owing to thermal expansion are considered. In particular, since usage of the objective at high temperature is out of specification of the manufacturer, it is preferable to keep the temperature to a room temperature as far as possible.

On the other hand, the local temperature control is a method of controlling temperature by directly contacting a heating or cooling device with a part to be temperature-controlled. Accordingly, thermal expansion of the objective, which is considered in the air temperature control, does not occur. Although the local temperature control is inferior in temperature stability to the air temperature control, the local temperature control has characteristics that it takes short time to reach a certain temperature and that this is capable of controlling temperatures of 60° C. or more. For instance, in a case where it is required to change temperatures between enzymatic reaction and cleaning or a case of using a high heat resistant enzyme, the local temperature control system is more suitable than the air temperature control.

However, as described above, as to constraints on the local temperature control using a prism type total internal reflection microscope, the prism is arranged immediately above the measurement substrate and the objective exists below the measurement substrate typically separated by 0.5 mm or less via immersion oil. Accordingly, the method of installing the local temperature controller is required to be managed. As such a method, a method of controlling temperature from both sides of the measurement substrate kept aside from the prism and the objective, and a method of control temperature directly on the prism can be considered. However, these methods are inefficient in view of thermal conductivity, and control is difficult at high temperatures.

As another method of solving these points, there is a method of arranging the local temperature controller between the prism and the measurement substrate. Since it is required to keep the separation between the objective and the measurement substrate within 0.5 mm, it is practically difficult to arrange the local temperature controller in this separation. There is no constraint on the separation between the prism and the measurement substrate. However, it is preferable that the local temperature controller have a refractive index close to that of the prism and be made of a highly transparent material, in order to generate evanescent waves after light passes through the local temperature controller. The prism is typically made of quarts. Accordingly, a glass heater can be considered as an example of the local temperature controller. Since the glass heater is transparent, it is also preferable to be able to observe a flow path.

The glass heater includes a transparent conductive film formed by vapor deposition on heat-resistant glass, and generates heat by being energized. The glass heater has characteristics capable of acquiring a large amount of heat with low power consumption while transparency and corrosion resistance of glass remain as they are. The glass heater has high thermal responsiveness, and is capable of quick following even a large variation in temperature. A thin film semiconductor mainly including indium oxide or tin oxide and containing graphite, chromium, nickel or the like is mainly adopted as the transparent conductive film. For instance, there is a glass heater in which a strong transparent conductive film with a width of 2000 to 7000 angstrom is coated on the heat-resistant glass by the chemical vapor deposition method at high temperature. Electrodes are attached to form a glass heater, and energization causes the transparent conductive film to generate heat. Thus, the glass heater is a high temperature heating glass heater having transparency and conductivity. The deposited film is energized, thereby generating Joule heat due to the resistance. The deposition is made so as to equalize the film thickness at nano level. Accordingly, heating with smaller temperature gradient can be realized. Since the conductive film is not changed by being submersed in aqua regia, the heater can be used semipermanently unless the heater is damaged. However, in a case where the film thickness varies according to the place, there is a danger that abrupt variations in temperature crack the heater.

As a result of single molecule measurement with arranging the local temperature controller between the prism and the measurement substrate, the inventors have found that, because the indium oxide and the tin oxide, which are ingredients of the transparent conductive film of the glass heater emit intrinsic fluorescence at positions of incident and reflected light, single molecule fluorescence from the measurement substrate cannot be observed. Intensities of fluorescence at 488 nm of fused silica with a thickness of 1 mm and the glass heater were measured to be 0.006 and 0.316, respectively, using a fluorometer. The glass heater exhibited around a 50 times higher background. Accordingly, since a typical fused glass has low intrinsic fluorescence, single molecule fluorescence can be observed. However, in a case of using the glass heater, it is difficult to observe single molecule fluorescence unless intrinsic fluorescence from the heater is avoided.

An object of the present invention relates to observation of single molecule fluorescence while temperature of a sample solution is controlled by a temperature controller and intrinsic fluorescence of the temperature controller is avoided, in a total internal reflection microscope.

Solution to Problem

The present invention relates to provision of an opening at the areas of a temperature controller through which incident light and reflected light pass, and configuration adopting a material with intrinsic fluorescence lower than that of the other parts, in a total internal reflection microscope including a prism and the temperature controller.

Advantageous Effects of Invention

The present invention enables intrinsic fluorescence of the temperature controller to be suppressed, which allows highly sensitive fluorescence observation while controlling sample solution temperature with high precision. For instance, this in turn allows the throughput of single molecule DNA sequencing using a total internal reflection microscope to be improved.

BRIEF DESCRIPTION OF DRAWINGS

FIG. 4 is a partially enlarged sectional view of a local temperature controller in Embodiment 3.

DESCRIPTION OF EMBODIMENTS

Figure 1:
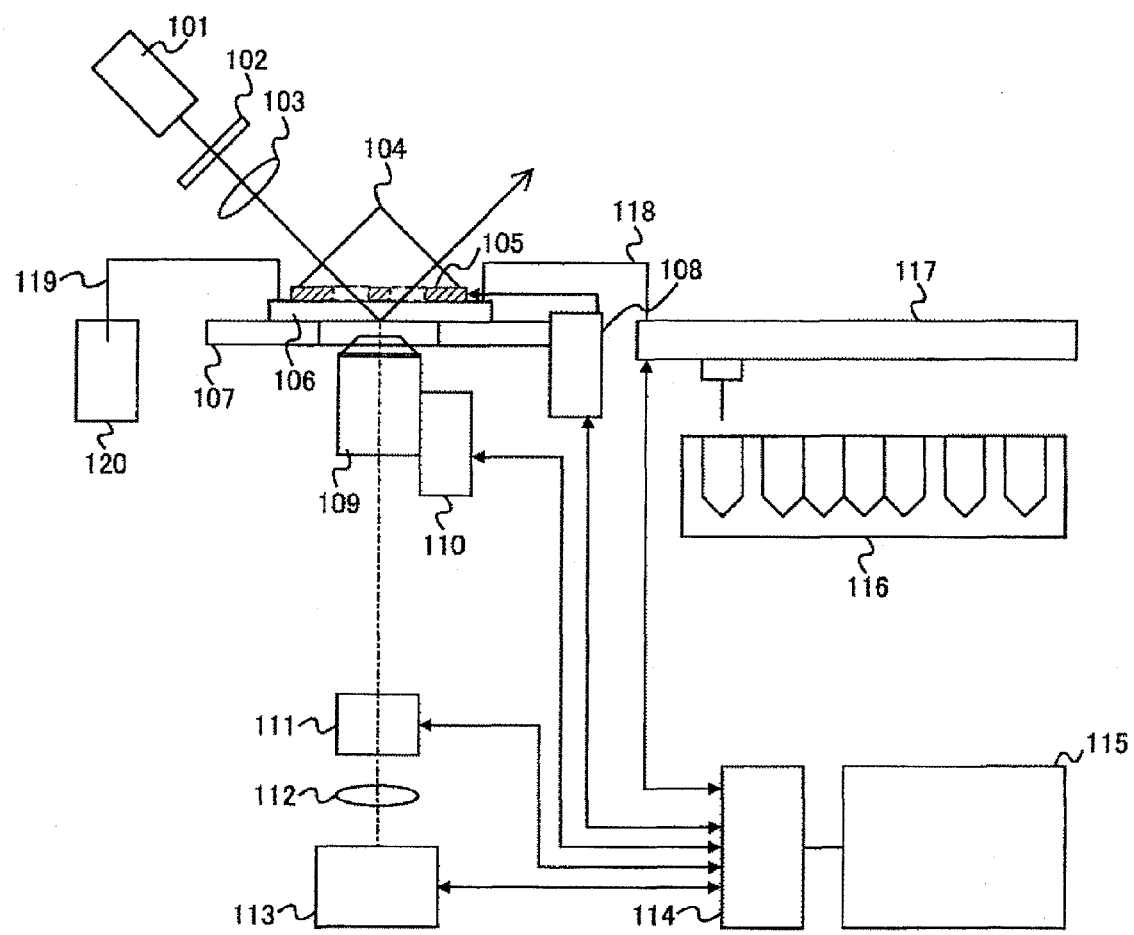
FIG. 1 shows a prism type total internal reflection microscope with a temperature control function in Embodiment 1.

An embodiment discloses that, in a prism type total internal reflection microscope, in order to prevent single molecule observation from being incapable owing to a laser beam passing through ingredients of a transparent conductive film of a local temperature controller emitting intrinsic fluorescence, temperature is controlled by contacting a local temperature controller that has a heating or cooling function and includes openings at areas through which incident light and reflected light pass, with a substrate to be measured. The embodiment also discloses that an area corresponding to an opening is configured by a material with lower intrinsic fluorescence in comparison with the other areas of the temperature controller.

An embodiment discloses a total internal reflection microscope apparatus including a substrate holding a fluorescent sample solution, a prism, an excitation light source emitting excitation light, and measuring instrument detecting fluorescence, wherein a temperature controller is arranged between the prism and the substrate, and the excitation light having passed through the prism and the temperature controller and incident onto the substrate is totally internally reflected at a boundary between the substrate and the sample solution, and areas of the temperature controller through which incident light and reflected light of the excitation light pass are made of a material with an intrinsic fluorescence lower than that of other areas.

An embodiment discloses a method for analyzing a fluorescent sample, including: preparing a total internal reflection microscope apparatus in which a temperature controller is arranged between a prism and a substrate; holding a fluorescent sample solution on the substrate; emitting excitation light so as to pass through the prism and the temperature controller and be incident onto the substrate and totally internally reflected at a boundary between the substrate and the sample solution; and detecting fluorescence of the fluorescent sample solution, wherein areas of the temperature controller through which incident light and reflected light of the excitation light pass are made of a material with an intrinsic fluorescence lower than that of other areas.

An embodiment discloses that the total internal reflection microscope apparatus is configured for single molecule DNA sequencing.

An embodiment discloses that openings are provided at respective areas of the temperature controller through which the incident light and the reflected light pass, and a liquid or a solid with an intrinsic fluorescence lower than that of quartz is arranged at the openings.

An embodiment discloses that openings are provided at respective areas of the temperature controller through which the incident light and the reflected light pass, and glycerol is arranged at the openings.

An embodiment discloses that openings are provided at respective areas of the temperature controller through which the incident light and the reflected light pass, and a silicon resin is arranged at the openings.

An embodiment discloses that openings are provided at respective areas of the temperature controller through which the incident light and the reflected light pass, and PDMS is arranged at the openings.

An embodiment discloses that two openings are arranged at the respective areas of the temperature controller through which the incident light and the reflected light pass, and prisms are arranged at the respective openings.

An embodiment discloses that an integrated opening is provided at the areas of the temperature controller through which the incident light and the reflected light pass, and one prism is arranged at the opening.

An embodiment discloses that the temperature controller includes an optical transparent material having a conductive film or a conductive substance, and the conductive film or the conductive substance is arranged at areas other than the areas through which the incident light and the reflected light pass.

An embodiment discloses that the temperature controller is a glass heater including a transparent conductive film, and a transparent conductive film is not arranged at the areas of the glass heater through which the incident light and the reflected light pass.

An embodiment discloses that the temperature controller is a glass heater including a transparent conductive film.

An embodiment discloses that the temperature controller includes a rubber heater, a hot wire heater or a film heater.

An embodiment discloses that openings are provided at respective areas of the temperature controller through which the incident light and the reflected light pass, and diameters of the openings are equal to or less than φ10 mm.

An embodiment discloses that an integrated opening is provided at the areas of the temperature controller through which the incident light and the reflected light pass, and vertical and horizontal sizes of the opening are 1 to 10 mm and 4 to 40 mm, respectively.

An embodiment discloses that the apparatus further includes a stage holding the substrate, the stage being driven independently from the temperature controller.

An embodiment discloses that the excitation light is a laser beam.

The aforementioned and other novel characteristics and advantageous effects of the present invention will hereinafter be described with reference to drawings. The figures are used only for illustration. The figures do not limit the scope of the right. The embodiments can be appropriately combined.

Embodiment 1

FIG. 1 schematically shows a prism type total internal reflection microscope having a local temperature control function. This microscope is a total internal reflection microscope, and controls temperature by contacting a heating or cooling device having openings at areas of incident light and reflected light with a substrate to be measured.

A laser beam oscillated by a laser 101 is circularly polarized by a λ/4 wavelength plate 102, passes through a condenser lens 103 and subsequently is perpendicularly incident onto a prism 104. As a glass for the prism, an optical glass that can be manufactured with very high homogeneity is required. Accordingly, synthetic silica or BK7 or BSC7 with high transmittance and high homogeneity is generally adopted.

The laser beam passes through an area of an opening formed on a local temperature controller 105, which is temperature-controlled by a local temperature controller controlling unit 108, and then is incident onto a refractive index boundary surface of a measurement substrate 106, i.e., a boundary between the measurement substrate 106 and solution, disposed on a measurement substrate stage 107, at incident angle of approximately 68°. The laser beam is totally internally reflected, thereby generating evanescent waves. The area of opening of the local temperature controller 105 are filled with glycerol, whose refractive index close to that of the prism 104, thereby preventing the laser beam from totally internally reflected at the prism 104 and the area of the opening of the local temperature controller 105. Because of an analogous reason, glycerol is filled between the local temperature controller 105 and the measurement substrate 106. Although the glycerol is a liquid with a high viscosity, the glycerol easily leaks from the opening to the measurement substrate 106. In case where only a small air layer is formed between the prism 104 and the area of the opening of the local temperature controller 105, the laser beam is totally internally reflected by this layer. As a method of preventing this, it can be considered that the opening of the local temperature controller 105 is blocked by a liquid material with low intrinsic fluorescence and subsequently the liquid material is solidified. Among such materials is, for instance, PDMS, which is a silicon resin. Since PDMS is an elastic material, the air layer can be eliminated by pushing PDMS against the prism 104 and the measurement substrate 106. This negates the need to use glycerol, thereby facilitates installation of the measurement substrate 106 and further is advantageous to automate the apparatus. Moreover, there is a method of preliminarily forming the area corresponding to the opening in a material of low intrinsic fluorescence. For instance, in a case of forming the transparent conductive film of the glass heater by a chemical vapor deposition method at high temperature, the positions corresponding to areas where the laser beam is incident onto the local temperature controller 105 and reflected out are preliminarily masked so as not to be applied with a deposited film, and thus forms the local temperature controller 105, thereby preventing indium oxide or tin oxide, a major factor of intrinsic fluorescence, from being irradiated with the laser beam. Also in a system of controlling temperature by running minute conductive wiring instead of a transparent conductive film, avoidance of the wiring from the areas corresponding to the openings enables intrinsic fluorescence to be reduced. This allows fluorescence single molecule observation.

In an evanescent field, excitation light exponentially decays in intensity with increasing separation from the refractive index boundary surface, and the excitation light intensity becomes 1/e (e is the natural logarithm) at a distance at and around 50 to 150 nm. The present system allows a volume irradiated with the excitation light to be significantly reduced in comparison with epifluorescence detection, thereby enabling background light, starting with fluorescence emission from free phosphors suspending in solution and Raman scattering of water, to be significantly reduced. Fluorescence of evanescent waves passes through the objective 109, which is focused by the Z-axis stage 110 for the objective, further passes through the filter unit 111, by which unnecessary wavelength components are removed, and passes through the imaging lens 112 to form an image on a CCD 113, which is a two-dimensional detector. A signal of the formed image is processed by a control PC 114, and the result is displayed on a monitor 115.

This apparatus further includes a mechanism capable of flowing a reagent, having been sucked by a dispensing unit 117 from a reagent container 116, via a flowing tube 118, in parallel with the refractive index boundary surface of the measurement substrate 106. This allows flowing different reagents continuously. The flowed reagent passes through a waste fluid tube 119 and is collected in a waste fluid vessel 120.

As a temperature control device for a microscope that includes an opening, a device controlling the temperature of a measurement substrate arranged in the microscope by controlling the temperature of a microscope stage itself that includes an opening of approximately ϕ20 to 50 for allowing an objective to approach, has already appeared on the market. It can be said that this is a system of controlling the temperature of the measurement substrate stage 107 in FIG. 1.

Differences between the ready-made article and this embodiment can be broadly summarized into following three points.

A first point is that the opening of the ready-made article has a large diameter of at least ϕ20. This is because an object of providing the opening is to allow the objective to approach a measurement substrate. Accordingly, it is inevitably required to provide an opening equal to or larger than the diameter of the objective. On the other hand, since this embodiment has an object to reduce intrinsic fluorescence, it is sufficient to provide the opening only at areas of the temperature controller through which the incident light and the reflected light of the laser beam pass. The diameter of the laser beam is approximately one millimeter. Accordingly, a few millimeters are sufficient for the diameter of the opening. There is no temperature controller that is included in the ready-made article and has an opening of a few millimeters.

A second point is that efficiency of controlling temperature of the ready-made article is low. Since it is required for the ready-made article to provide an opening of at least ϕ20 so as to allow the objective to approach, the distance to the scope of the microscope (the center of the opening) is at least 10 mm. Provided that the thickness of the measurement substrate 106 is 1 mm, which is identical to that of the slide glass, adverse effects owing to thermal diffusion from both sides of the measurement substrate 106 are large and thereby the amount of heat to be transmitted to the center of the scope becomes significantly small. Accordingly, the temperature distribution abruptly decreases with approaching the center of the scope. The inventors have found that, in a case of controlling temperature of at least 60° C., it is required to keep the temperature of the stage to 90 to 100° C. In consideration that adverse effects owing to the thermal expansion of the device such as the stage is estimated to be large and in view of safety, this system is not preferable. On the other hand, in this embodiment, local temperature controller 105 can control temperature immediately above the measurement substrate 106. Accordingly, this is characterized in that heat transfer efficiency is significantly high and temperature responsiveness is significantly high. The inventors have found that, in a case where the measurement substrate has a thickness of 1 mm, the temperature difference between the glass heater and the measurement substrate is equal to or lower than five degrees.

Further, the inventors have confirmed that, since the opening has a small diameter of a few millimeters, there is substantially no temperature difference between areas where the opening is provided and the other areas.

A third point is that, in the ready-made article, since the stage also serves as the temperature controller, the measurement substrate is integrated with the stage. Accordingly, in a case of observing a different scope, it is required to move the measurement substrate by moving the stage, and the scope of the microscope inevitably deviates from the center of the opening. Thus, the temperature of the scope of the microscope is not constant; the closer to the periphery of the opening, the higher the temperature becomes. Accordingly, in a case where the temperature largely affects the reaction, it is difficult to apply this system. In order to keep the temperature of the scope of the microscope constant while moving the stage, the measurement substrate is required to be temporarily separated from the stage. On the other hand, in this embodiment, since the measurement substrate stage 107 and the local temperature controller 105 are subject to different control systems, the stage and the controller can be separately be moved. Accordingly, the scope of the microscope can always be set to a specific position on the local temperature controller 105 by moving only the measurement substrate stage 107, thereby allowing observation at the same temperature.

Figure 2:
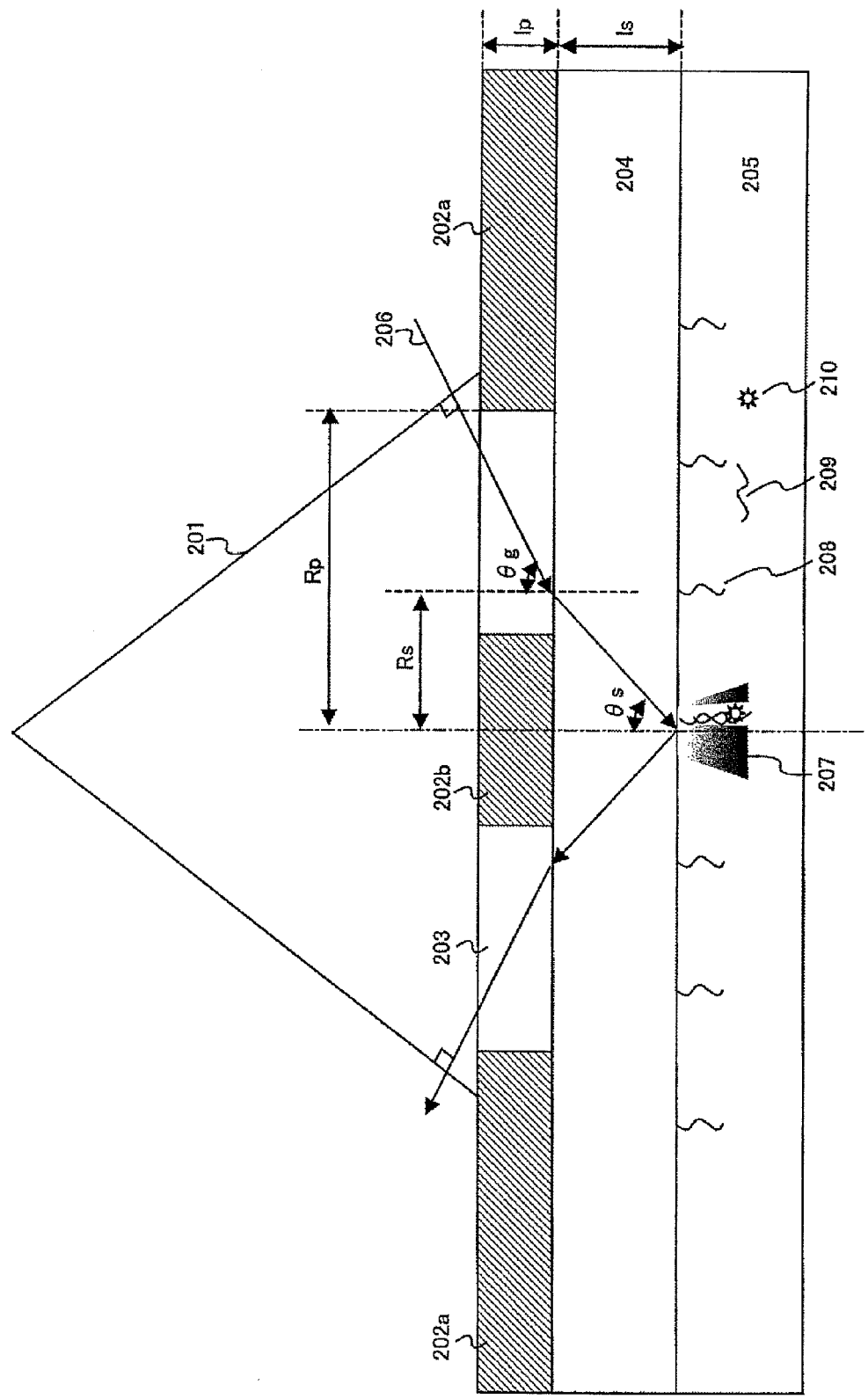
FIG. 2 is a partially enlarged sectional view of a local temperature controller in Embodiment 1.

Referring to FIG. 2, processes of single molecule DNA sequencing will be described. FIG. 2 shows an enlarged view of the prism 104, the local temperature controller 105 and the measurement substrate 106 in FIG. 1 in detail. The reagent is supplied using the flow system shown in FIG. 1. Unless otherwise specified, the temperature controller 105 is kept at 25° C. and an experiment is performed.

A biotinylated primer 208 is immobilized on a side of the solution on the refractive index boundary between the measurement substrate 204 and the solution 205 via binding of biotin-BSA and streptavidin. Next, the target nucleic acid 209 to be sequenced is flowed to be hybridized with the biotinylated primer. This forms double strand nucleic acid of the biotinylated primer 208 and the target nucleic acid 209. Unreacted reagents are removed by cleaning using lavage fluid, such as tris buffers, between processes. Next, the temperature controller 105 in FIG. 1 is set to 37° C., adopts T4 DNA polymerase and Cy3-dNTP210 (one type of nucleotide dNTP (N is any one of A, C, G and T) labeled with Cy3) and then, only in a case where a complementary strand can be formed with respect to the target nucleic acid 209, the Cy3-dNTP molecule is taken into the elongating strand of the biotinylated primer 208.

After the elongation reaction is finished and the temperature controller 105 in FIG. 1 is set to 60° C. and unreacted Cy3-dNTP is removed by lavage fluid, the temperature controller 105 in FIG. 1 is returned to 25° C. Subsequently, as a laser for detecting elongating Cy3-dNTP, a laser beam oscillated from an argon laser 206 (wavelength: 514.5 nm) is perpendicularly incident onto the prism 201, passes through the glycerol 203 filled in the opening on the local temperature controller 202, and totally internally reflected at the refractive index boundary between the measurement substrate 204 and the solution 205.

The area of the opening on the local temperature controller 202 is filled with the glycerol 203 with the refractive index close to that of the prism 201, thereby preventing the laser beam from being totally internally reflected at the prism 201 and the area of the opening on the local temperature controller 202. According to an analogous reason, glycerol is also filled between the local temperature controller 202 and the measurement substrate 204.

When the laser beam is totally internally reflected at the refractive index boundary, Cy3 is excited by the evanescent waves 207 and thereby detectable by fluorescence detection at the binding position of the target nucleic acid. After verification of the position of Cy3, Cy3 is irradiated with high power excitation light and the fluorescence is faded. Accordingly, fluorescence emission thereafter is suppressed. The above dNTP elongation reaction is stepwise repeated such that the types of nucleotides are A→G→C→T→A, thereby allowing nucleotide sequence of the target nucleic acid molecule to be determined. Further, the target DNA is immobilized within the scope for fluorescence detection, and the above elongation reaction is processed in parallel, thereby allowing the target nucleic acids to be simultaneously sequenced.

The local temperature controller 202 in FIG. 2 adopts the configuration that the openings are provided at the areas through which the incident light and the reflected light pass. The diameters of the openings through which the incident light and the reflected light pass are calculated by the thickness is of the measurement substrate 204, the thickness lp of the local temperature controller 202, the incident light angle θg onto the boundary between the measurement substrate 204 and the local temperature controller 202, the transmitted light angle θs with respect to the boundary between the measurement substrate 204 and the local temperature controller 202, the refractive index of the glycerol 203, the refractive index of the measurement substrate 204, and the refractive index of the solution 205. According to Snell's law, θs is set to an angle at which total internal reflection occurs, thereby allowing θg to be uniquely determined. Therefore, $Rs = ls \cdot \tan \theta s$, $Rp = lp \cdot \tan \theta g + Rs$.

In a case where the refractive index of the glycerol 203 is 1.47, the refractive index of the solution 205 is 1.33, the thickness is of the measurement substrate 204 is 1 mm, the thickness lp of the local temperature controller 202 is 1 mm, Rs and Rp when the refractive index of the measurement substrate 204 is changed from 1.47 to 1.78 are calculated as follows by substitution into the above equation.

TABLE 1

| | Refractive index of measurement substrate 204 | | | | | |
|---|---|---|---|---|---|---|
| | 1.47 | 1.50 | 1.55 | 1.60 | 1.66 | 1.78 |
| Rs(mm) | 2.124 | 1.917 | 1.671 | 1.495 | 1.339 | 1.124 |
| Rp(mm) | 4.433 | 4.226 | 3.980 | 3.804 | 3.648 | 3.433 |

In a case where, for instance, the refractive index of the measurement substrate 204 is 1.47 with assumption of the slide glass, the minimum value of the diameter of the opening of each of the areas of the incident light and the reflected light is 4.433−2.124=2.309 mm. However, in actuality, it is required to widen the diameter of the opening in consideration of spreading of the laser beam. Provided that the diameter of the beam is 1 mm, the diameter of the opening is set to approximately 4 mm, thereby preventing the laser beam from being incident onto the local temperature controller 202. It is sufficient that the diameter of the opening in the vertical direction in the page space be larger than the diameter of the laser beam. This diameter of at least 1 mm prevents the laser beam from being incident onto the local temperature controller 202. Accordingly, it is sufficient that the openings of the diameters of 1 mm×4 mm reside at two points corresponding to the areas through which the incident light and the reflected light pass.

In a case where the refractive index of the measurement substrate 204 is 1.47, the diameter of the local temperature controller 202b is 2×Rs and 4.248 mm at the maximum. Since the local temperature controller 202b is arranged immediately above the evanescent waves 207, advantageous effects of temperature control are improved. On the other hand, in a system of controlling temperature of the microscope stage itself, since the opening of ϕ20 to 50 is provided in order to allow the objective to approach, there is no heater immediately above the evanescent waves 207.

Further, the diameters and the positions of the openings are determined according to the thickness ls of the measurement substrate 204, the thickness lp of the local temperature controller 202 and the like. Accordingly, these details can be adapted to conditions for facilitating manufacturing the openings. For instance, in a case where the thickness lp of the local temperature controller 202 and the thickness ls of the measurement substrate 204 are fixed, the diameters and the positions of the openings can be adjusted by filling a certain thickness of the glycerol 203 between the measurement substrate 204 and the local temperature controller 202.

In FIG. 2, the openings of the local temperature controller 202 may be the two for the incident light and the reflected light. Instead, the two openings may be integrated by removing a part 202b. In a case where the refractive index of the measurement substrate 204 is 1.47, the diameter of the integrated opening is 8.866 mm according to 2×Rp. In consideration of spreading of the laser beam, the diameter of the opening becomes approximately 10 mm. Accordingly, the diameter of the opening becomes approximately 1 mm×10 mm.

In a system of providing the opening, it is sufficient that the opening be filled with the glycerol 203. Accordingly, the material of the local temperature controller may be not only glass but also an opaque material. Accordingly, the controller can be replaced with a rubber heater, a hot wire heater, a film heater or the like. The part of the glycerol 203 may be replaced with glass, PDMS, plastic or the like.

Embodiment 2

In this embodiment, two prisms are embedded in two areas of openings in the local temperature controller instead of the glycerol. Hereinafter, differences from Embodiment 1 will be principally described.

Figure 3:
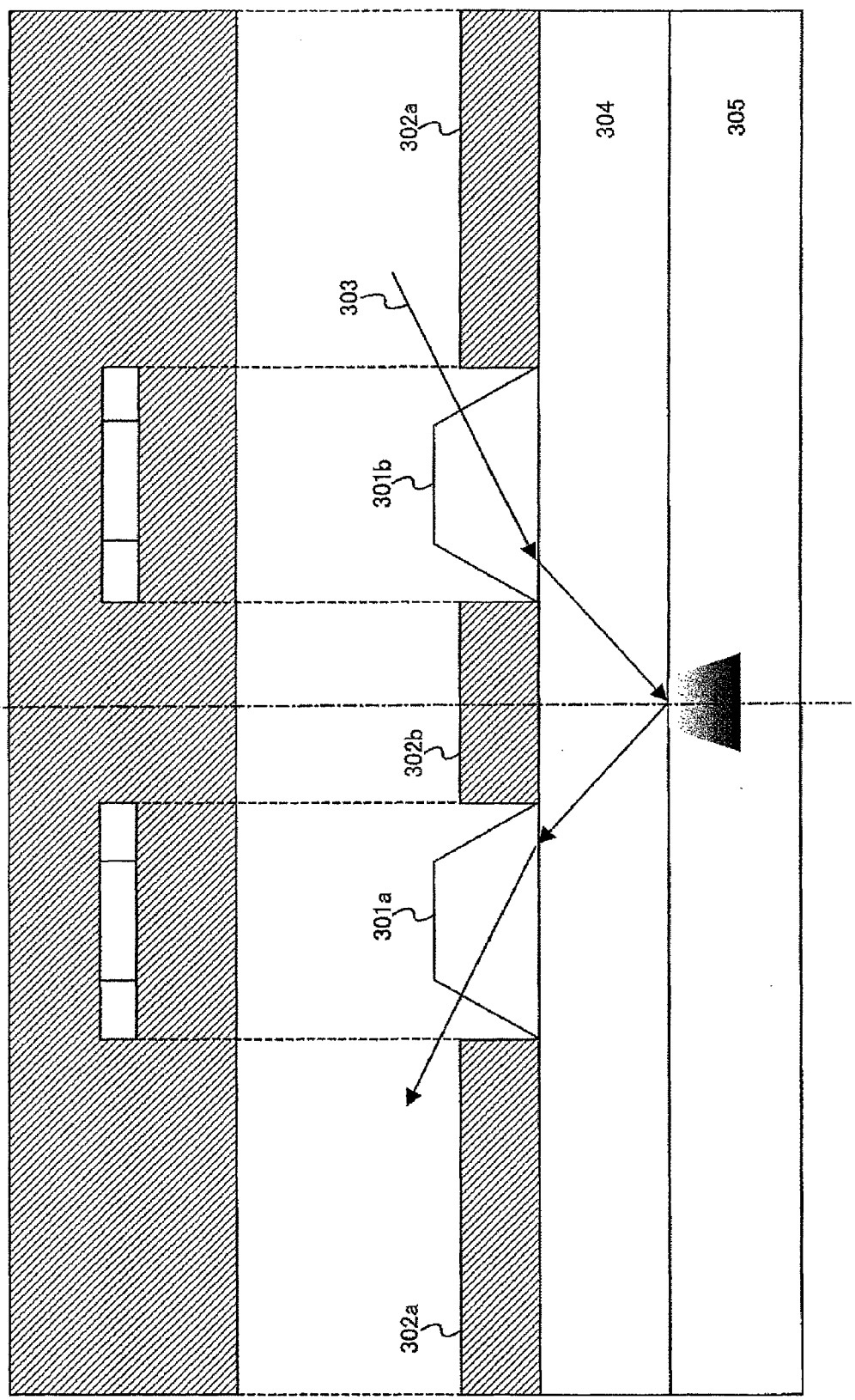
FIG. 3 is a partially enlarged sectional view of a local temperature controller in Embodiment 2.

In this embodiment, as shown in FIG. 3, two prisms 301 are embedded in the respective two areas of the openings of the local temperature controller 302. The prisms 301 are intimately contact with the measurement substrate 304. It is preferable that the size of the prism be approximately from 1 mm×4 mm to 4 mm×40 mm. When the laser beam 303 is perpendicularly incident onto the prism 301, since the prism 301 is intimately contact with the measurement substrate 304, totally internally reflection occurs between the measurement substrate 304 and the solution 305 without use of the glycerol.

Embodiment 3

In this embodiment, one prism is embedded in one area of an opening of a local temperature controller instead of the glycerol. Hereinafter, a difference from Embodiments 1 and 2 will be principally described.

In this embodiment, as shown in FIG. 4, a prism 401 is embedded in one area of an opening of a local temperature controller 402. It is preferable that the size of the prism be approximately from 1 mm×10 mm to 4 mm×40 mm. When the laser beam 403 is perpendicularly incident onto the prism 401, since the prism 401 is intimately contact with the measurement substrate 404, totally internally reflection occurs between the measurement substrate 404 and the solution 405 without use of glycerol.

REFERENCE SIGNS LIST

| | |
|---|---|
| 101 | laser |
| 102 | λ/4 wavelength plate |
| 103 | condenser lens |
| 104, 201, 301, 401 | prism |
| 105 | temperature controller |
| 106, 204, 304, 404 | measurement substrate |
| 107 | measurement substrate stage |
| 108 | local temperature controller controlling unit |
| 109 | objective |
| 110 | Z-axis stage for the objective |
| 111 | filter unit |
| 112 | imaging lens |
| 113 | CCD |
| 114 | control PC |
| 115 | monitor |
| 116 | reagent container |
| 117 | dispensing unit |
| 118 | flowing tube |
| 119 | waste fluid tube |
| 120 | waste fluid vessel |
| 202, 302, 402 | local temperature controller |
| 203 | glycerol |
| 205, 305, 405 | solution |
| 206 | argon laser |
| 207 | evanescent waves |
| 208 | biotinylated primer |
| 209 | target nucleic acid |
| 210 | Cy3-dNTP |
| 303, 403 | laser beam |

The invention claimed is:

1. A total internal reflection microscope apparatus comprising a substrate holding a fluorescent sample solution, a prism, an excitation light source emitting excitation light, and measuring instrument detecting fluorescence,
    wherein a temperature controller is arranged between the prism and the substrate, and the excitation light having passed through the prism and the temperature controller and incident onto the substrate is totally internally reflected at a boundary between the substrate and the sample solution, and
    areas of the temperature controller through which incident light and reflected light of the excitation light pass are made of a material with an intrinsic fluorescence lower than that of other areas.

2. The total internal reflection microscope apparatus according to claim 1,
    wherein the apparatus is configured for single molecule DNA sequencing.

3. The total internal reflection microscope apparatus according to claim 1,
    wherein openings are provided at respective areas of the temperature controller through which the incident light and the reflected light pass, and a liquid or a solid with an intrinsic fluorescence lower than that of quartz is arranged at the openings.

4. The total internal reflection microscope apparatus according to claim 1,
    wherein openings are provided at respective areas of the temperature controller through which the incident light and the reflected light pass, and glycerol is arranged at the openings.

5. The total internal reflection microscope apparatus according to claim 1,
wherein openings are provided at respective areas of the temperature controller through which the incident light and the reflected light pass, and a silicon resin is arranged at the openings.

6. The total internal reflection microscope apparatus according to claim 1,
wherein openings are provided at respective areas of the temperature controller through which the incident light and the reflected light pass, and PDMS is arranged at the openings.

7. The total internal reflection microscope apparatus according to claim 1,
wherein two openings are arranged at the respective areas of the temperature controller through which the incident light and the reflected light pass, and prisms are arranged at the respective openings.

8. The total internal reflection microscope apparatus according to claim 1,
wherein an integrated opening is provided at the areas of the temperature controller through which the incident light and the reflected light pass, and one prism is arranged at the opening.

9. The total internal reflection microscope apparatus according to claim 1,
wherein the temperature controller comprises an optical transparent material having a conductive film or a conductive substance, and the conductive film or the conductive substance is arranged at areas other than the areas through which the incident light and the reflected light pass.

10. The total internal reflection microscope apparatus according to claim 1,
wherein the temperature controller is a glass heater including a transparent conductive film, and a transparent conductive film is not arranged at the areas of the glass heater through which the incident light and the reflected light pass.

11. The total internal reflection microscope apparatus according to claim 1,
wherein the temperature controller is a glass heater including a transparent conductive film.

12. The total internal reflection microscope apparatus according to claim 1,
wherein the temperature controller comprises a rubber heater, a hot wire heater or a film heater.

13. The total internal reflection microscope apparatus according to claim 1,
wherein openings are provided at respective areas of the temperature controller through which the incident light and the reflected light pass, and diameters of the openings are equal to or less than $\phi 10$ mm.

14. The total internal reflection microscope apparatus according to claim 1,
wherein an integrated opening is provided at the areas of the temperature controller through which the incident light and the reflected light pass, and vertical and horizontal sizes of the opening are 1 to 10 mm and 4 to 40 mm, respectively.

15. The total internal reflection microscope apparatus according to claim 1,
further comprising a stage holding the substrate, the stage being driven independently from the temperature controller.

16. The total internal reflection microscope apparatus according to claim 1,
wherein the excitation light is a laser beam.

17. A method for analyzing a fluorescent sample, comprising:
preparing a total internal reflection microscope apparatus in which a temperature controller is arranged between a prism and a substrate;
holding a fluorescent sample solution on the substrate;
emitting excitation light so as to pass through the prism and the temperature controller and be incident onto the substrate and totally internally reflected at a boundary between the substrate and the sample solution; and
detecting fluorescence of the fluorescent sample solution,
wherein areas of the temperature controller through which incident light and reflected light of the excitation light pass are made of a material with an intrinsic fluorescence lower than that of other areas.

* * * * *